US008406084B2

(12) United States Patent
Buccafusca et al.

(10) Patent No.: US 8,406,084 B2
(45) Date of Patent: Mar. 26, 2013

(54) TRANSDUCER DEVICE HAVING COUPLED RESONANT ELEMENTS

(75) Inventors: Osvaldo Buccafusca, Fort Collins, CO (US); Steven Martin, Fort Collins, CO (US)

(73) Assignee: Avago Technologies Wireless IP (Singapore) Pte. Ltd., Singapore (SG)

( * ) Notice: Subject to any disclaimer, the term of this patent is extended or adjusted under 35 U.S.C. 154(b) by 490 days.

(21) Appl. No.: 12/622,598

(22) Filed: Nov. 20, 2009

(65) Prior Publication Data

US 2011/0122731 A1    May 26, 2011

(51) Int. Cl.
*B06B 1/00*    (2006.01)

(52) U.S. Cl. ......... 367/176; 367/162; 310/322; 310/334

(58) Field of Classification Search .......... 367/154, 367/162, 176; 310/322, 328, 334
See application file for complete search history.

(56) References Cited

U.S. PATENT DOCUMENTS

| | | | | |
|---|---|---|---|---|
| 4,006,371 A | * | 2/1977 | Quirke | 310/322 |
| 4,700,100 A | * | 10/1987 | Congdon et al. | 310/332 |
| 6,049,158 A | * | 4/2000 | Takeuchi et al. | 310/328 |
| 6,140,740 A | * | 10/2000 | Porat et al. | 310/322 |
| 7,477,572 B2 | | 1/2009 | Caronti et al. | |
| 2008/0101625 A1 | | 5/2008 | Fazzio et al. | |
| 2008/0122317 A1 | | 5/2008 | Fazzio et al. | |
| 2008/0122320 A1 | | 5/2008 | Fazzio et al. | |
| 2008/0240482 A1 | | 10/2008 | Haddad et al. | |
| 2009/0140609 A1 | | 6/2009 | Huang | |
| 2009/0158851 A1 | | 6/2009 | Song et al. | |
| 2010/0214716 A1 | * | 8/2010 | Liu et al. | 361/290 |

OTHER PUBLICATIONS

Ch. Papageorgiou et al., "Modification of Resonance Characteristics of Ultrasonic Transducers by the Driving Circuit", Proceedings, XVII IMEKO World Congress, Jun. 22-27, 2003, pp. 603-608.
Related to co-pending U.S. Appl. No. 12/430,966, filed Apr. 28, 2009.

* cited by examiner

*Primary Examiner* — Ian Lobo

(57) ABSTRACT

A transducer device includes a coupling cavity, a first resonant element and a second resonant element. The first resonant element is coupled to the coupling cavity and configured to send or receive acoustic signals. The second resonant element is coupled to the coupling cavity and configured to modify a frequency response of the first resonant element via the coupling cavity.

18 Claims, 9 Drawing Sheets

TRANSDUCER DEVICE HAVING COUPLED RESONANT ELEMENTS

BACKGROUND

Generally, acoustic transducers convert received electrical signals to acoustic signals when operating in a transmit mode, and/or convert received acoustic signals to electrical signals when operating in a receive mode. The functional relationship between the electrical and acoustic signals of an acoustic transducer depends, in part, on the acoustic transducer's operating parameters, such as natural or resonant frequency, acoustic receive sensitivity, acoustic transmit output power and the like.

Acoustic transducers are manufactured pursuant to specifications that provide specific criteria for the various operating parameters. Applications relying on acoustic transducers, such as piezoelectric ultrasonic transducers and electro-mechanical system (MEMS) transducers, for example, typically require precise conformance with these criteria. In certain ultrasonic applications, for example, in which acoustic systems use frequency or phase modulation schemes, the bandwidth of the acoustic transducer may be engineered to improve performance. For example, multiple transducers with different resonant frequencies may be arranged in an array, so that the overall response of the transducer array is the desired frequency response. However, multiple designs are required to address each implementation, which may be time consuming and expensive. Also, a transducer array may require a relatively large physical layout in order to achieve the desired frequency response.

SUMMARY

In a representative embodiment, a transducer device includes a coupling cavity and first and second resonant elements. The first resonant element is coupled to the coupling cavity and configured to send or receive acoustic signals. The second resonant element is coupled to the coupling cavity and configured to modify a frequency response of the first resonant element via the coupling cavity.

In another representative embodiment, a transducer device includes a first resonant element including a first membrane arranged on a substrate and a first transducer structure stacked on the first membrane, and a second resonant element including a second membrane arranged on the substrate. The transducer device further includes a common coupling cavity configured to couple acoustic signals from the first and second resonant elements. The second resonant element may also include a second transducer structure stacked on the second membrane.

In another representative embodiment, a transducer device includes a first resonant element, a second resonant element and a mechanical coupler. The first resonant element is positioned on a substrate over a first cavity and has a first frequency response. The second resonant element is positioned on the substrate over a second cavity adjacent to the first resonant element and has a second frequency response. The mechanical coupler is in contact with the first and second resonant elements, causing each of the first and second resonant elements to oscillate at frequencies other than the first and second frequency responses, respectively.

BRIEF DESCRIPTION OF THE DRAWINGS

The example embodiments are best understood from the following detailed description when read with the accompanying drawing figures. It is emphasized that the various features are not necessarily drawn to scale. In fact, the dimensions may be arbitrarily increased or decreased for clarity of discussion. Wherever applicable and practical, like reference numerals refer to like elements.

DETAILED DESCRIPTION

Figure 1A:
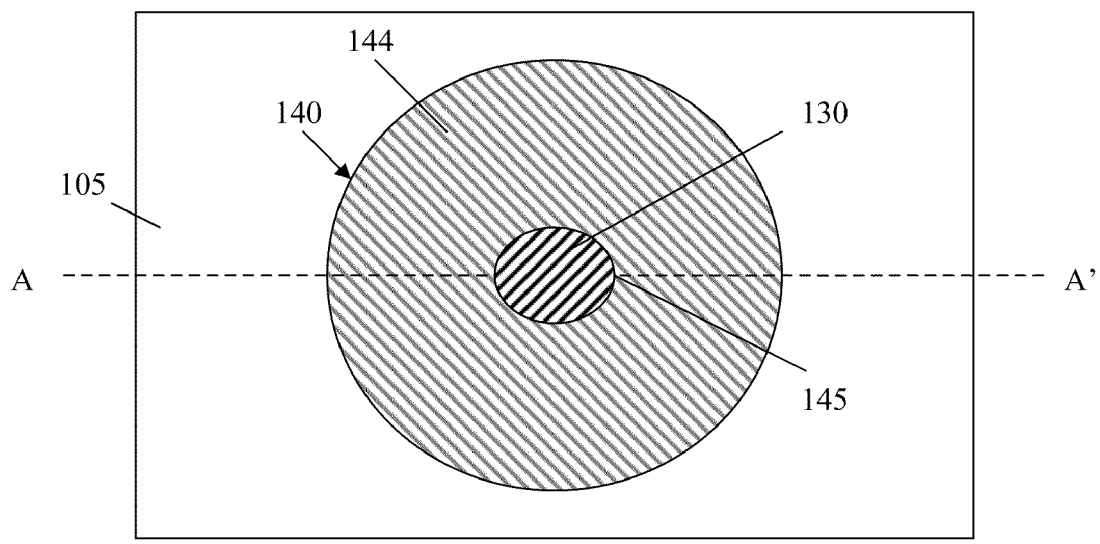
FIG. 1A is as top plan view illustrating a transducer resonant element of a coupled transducer device, according to a representative embodiment.

In the following detailed description, for purposes of explanation and not limitation, representative embodiments disclosing specific details are set forth in order to provide a thorough understanding of the present teachings. However, it will be apparent to one having ordinary skill in the art having had the benefit of the present disclosure that other embodiments according to the present teachings that depart from the specific details disclosed herein remain within the scope of the appended claims. Moreover, descriptions of well-known apparatuses and methods may be omitted so as to not obscure the description of the representative embodiments. Such methods and apparatuses are clearly within the scope of the present teachings.

Generally, it is understood that the drawings and the various elements depicted therein are not drawn to scale. Further, relative terms, such as "above," "below," "top," "bottom," "upper," "lower," "left," "right," "vertical" and "horizontal," are used to describe the various elements' relationships to one another, as illustrated in the accompanying drawings. It is understood that these relative terms are intended to encompass different orientations of the device and/or elements in addition to the orientation depicted in the drawings. For example, if the device were inverted with respect to the view in the drawings, an element described as "above" another element, for example, would now be "below" that element.

Likewise, if the device were rotated 90 degrees with respect to the view in the drawings, an element described as "vertical," for example, would now be "horizontal."

According to various embodiments, a coupled transducer device includes multiple resonant elements and a common coupling cavity for coupling the acoustic waves transmitted and/or received by the transducer device. The effect of the coupling cavity and the multiple resonant elements is to modify performance of one or more of the multiple resonant elements. The resonant elements may include multiple stacked transducer structures (two or more) arranged on thin plates or membranes that move or deform at predetermined frequencies. Alternatively, the resonant elements may include at least one transducer structure arranged on a membrane and at least one membrane (i.e., without a corresponding transducer structure). Also, according to various embodiments, a coupled transducer device includes multiple resonant elements and a mechanical coupling for coupling the acoustic waves transmitted and/or received by the transducer device. The coupled transducer device may be configured as an ultrasonic micro-electro-mechanical system (MEMS) device, for example.

A resonant transducer (e.g., one transducer structure) may be represented by a harmonic oscillator, for which displacement x is represented by Equation (1):

$$\frac{d^2 x}{dt^2} + \omega_0^2 x = 0 \quad (1)$$

Solving Equation (1), it is determined that $x = A \sin(\omega_0 t + \delta)$, where $\omega_0$ is resonant frequency, and A and $\delta$ are the amplitude and phase provided by the initial conditions.

When two harmonic oscillators (e.g., corresponding to two transducer structures) with the same resonant frequency are coupled together, the respective displacements x are represented by Equations (2) and (3), where the sub-index 1 and 2 refer to each harmonic oscillator and K is the coupling constant:

$$\frac{d^2 x_1}{dt^2} + \omega_0^2 x_1 + K^2 (x_1 - x_2) = 0 \quad (2)$$

$$\frac{d^2 x_2}{dt^2} + \omega_0^2 x_2 + K^2 (x_2 - x_1) = 0 \quad (3)$$

The general solution is in the form $x_i = A_1 \sin(\omega_1 t + \delta_1) + A_2 \sin(\omega_2 t + \delta_2)$ where i=1 or 2, $\omega_1^2 = \omega_0^2 + 2K^2$ and $\omega_2^2 = \omega_0^2$. Consequently either of the two harmonic oscillators will incorporate an additional frequency of oscillation due to the coupling of the other oscillator.

Applying this basic principle to coupled transducer devices, the acoustic response of each transducer (e.g., including the frequency, amplitude and/or phase of oscillation) is modified by coupling another transducer or resonant element, as discussed below. Hence, the coupling enables design and controlled manipulation of the responses of two (or more) transducers or other resonant elements.

In an embodiment, both of the transducers may be is driven to achieve motion in both transducers. However, in alternative embodiments, only one of the transducers may be driven to achieve motion in both transducers. When only one of the transducers is driven, the resonant frequencies of the two transistors may be the same or different. When the resonant frequencies are different, the solution for the coupled transducer device includes more frequencies. For example, in the general case in which the two harmonic resonators have different resonant frequencies $\omega_{01}$ and $\omega_{02}$, the general solution will involve frequencies represented by Equation (4):

$$\omega^2 = \omega_{01}^2 - \frac{(\omega_{01}^2 - \omega_{02}^2)}{2} + K^2 \pm \frac{\sqrt{(\omega_{01}^2 - \omega_{02}^2) + 4K^4}}{2} \quad (4)$$

Figure 1B:
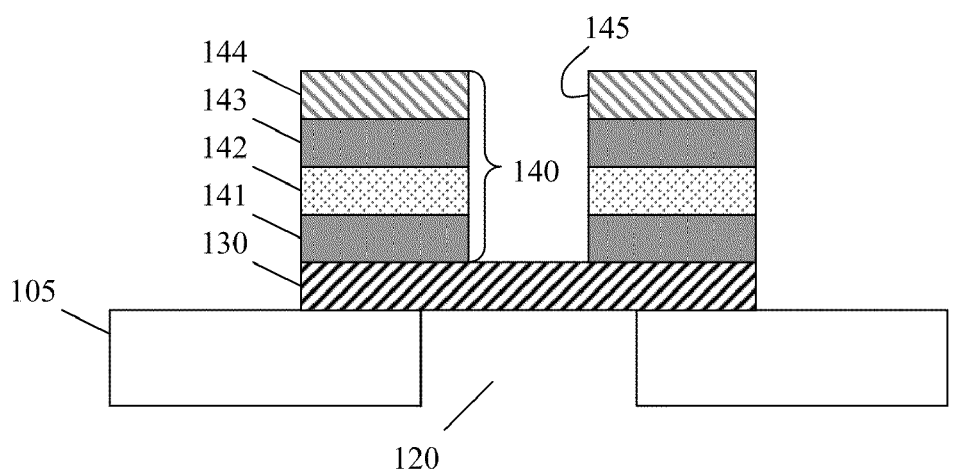
FIG. 1B is a cross-sectional diagram illustrating a transducer resonant element of a coupled transducer device, according to a representative embodiment.

FIG. 1A is as top plan view illustrating a resonant element of a coupled transducer device, which includes a stacked transducer structure, according to a representative embodiment. FIG. 1B is a cross-sectional diagram illustrating the resonant element of a coupled transducer device depicted in FIG. 1A, taken along line A-A', according to a representative embodiment.

Referring to FIGS. 1A and 1B, resonant element 110 includes substrate 105, on which thin plate or membrane 130 and transducer structure 140 are stacked. In the depicted embodiment, the membrane 130 and the transducer structure 140 are substantially circular in shape, and the transducer structure 140 forms an annular ring defining a center opening 145, through which a center portion of a top surface of the membrane 130 is exposed. In alternative embodiments, the membrane 130 and/or the transducer structure 140 may be formed in different shapes, such as ovals, squares, rectangles and the like, without departing from the scope of the present teachings. Likewise, the shapes of the membrane 130 and the transducer structure 140 may be different from one another. For example, a substantially circular transducer structure 140 may be formed on a substantially rectangular membrane 130, without departing from the scope of the present teachings.

As shown in FIG. 1B, the membrane 130 is positioned on the substrate 105 over a cavity 120, which enables the mechanical movement of the exposed portion of the membrane 130. The substrate 105 may be formed of various types of materials, including an insulating material, such as glass, sapphire, alumina or the like, or any semiconductor material compatible with semiconductor processes, such as silicon, gallium arsenide (GaAs), indium phosphide (InP) or the like. A semiconductor material is useful for integrating connections and electronics, thus reducing size and cost. The opening of the cavity 120 in the top surface of the substrate 105 is substantially circular, although it may have any of a variety of sizes and shapes, such as oval, square, rectangular and the like, without departing from the scope of the present teachings.

The membrane 130 may also be formed of various types of materials compatible with semiconductor processes, including polysilicon, silicon nitride, silicon carbide, boron silicate glass, or the like. The membrane 130 is thin enough to enable mechanical movement or vibrations in response to electrical and/or acoustic signals. For example, the membrane 130 may be about 0.5-2 microns thick at the exposed portion in order to vibrate at ultrasonic frequencies, although the thickness may vary to provide unique benefits for any particular situation or to meet application specific design requirements of various implementations, as would be apparent to one skilled in the art.

In the representative embodiment depicted in FIG. 1B, the transducer structure 140 includes multiple, stacked layers. In particular, a first electrode 141 is stacked on the top surface of the membrane 130, a piezoelectric layer 142 is stacked on a top surface of the first electrode 141, and a second electrode 143 is stacked on a top surface of the piezoelectric layer 142. The first and second electrodes 141 and 143 are formed of an electrically conductive material, such as molybdenum, tungsten or aluminum or the like, and the piezoelectric layer 142 is formed of a thin film of aluminum nitride (AlN), zinc oxide (ZnO), or other film compatible with semiconductor processes. The thicknesses of the electrodes and piezoelectric layers may range from about 0.1 microns to about 1.5 microns, for example. A passivation layer 144 may be optionally included on a top surface of the second electrode 143, in order to protect the other layers from humidity, debris and contaminants. The passivation layer 144 may be formed from silicon dioxide, silicon nitride, oxynitride, boron-silicate glass (BSG) or the like.

The first and second electrodes 141 and 143 are electrically connected to external circuitry via contact pads (not shown), which may be formed of a conductive material, such as gold, gold-tin alloy or the like. The contact pads may electrically connect with the first and second electrodes 141 and 143 through various electronic circuits (not shown), such as connectors passing through vias formed in the substrate 105 and/or the membrane 130, trace patterns and the like.

As discussed above, the first and second electrodes 141 and 143, the piezoelectric layer 142 and the passivation layer 144 may be substantially circular rings, which surround the suspended portion of the membrane 130. In alternative embodiments, the first electrode 141 and the piezoelectric layer 142 may not include an opening, but rather may be formed over the entire surface of the membrane 130. In this configuration, the top surface of the piezoelectric layer 142 is exposed through the opening in the transducer structure 140, as opposed to the top surface of the membrane 130, as shown in FIG. 1A. In a transmit mode (e.g., a speaker), an electrical input signal (e.g., excitation signal) may be input to the first and/or second electrodes 141 and 143, via corresponding contact pads, and converted to a mechanical vibration (or resonance) having a frequency induced by the piezoelectric layer 142 and/or the membrane 130. In a receive mode (e.g., a microphone), an acoustic input signal may be input to the piezoelectric layer 142 and/or the membrane 130 through the center opening 145 and/or the cavity 120, and converted to a corresponding electrical output signal output by the first and/or second electrodes 141 and 143, via the contact pads.

The resonant element 110 may be an ultrasonic transducer fabricated using MEMS technology, for example, known as a MEMS ultrasonic transducer (MUT). In this case, the membrane 130 moves or deforms at ultrasonic frequencies, which is translated into electrical signals available at the contact pads. In various embodiments, the translation may be made through a piezoelectric material (p-MUT), e.g., by the piezoelectric layer 144 and/or the membrane 130, or through a capacitance variation (c-MUT). It is understood that other types and arrangements of membranes and/or transducer structures may be incorporated in the resonant element 110, without departing from the scope of the present teachings.

Figure 2A:
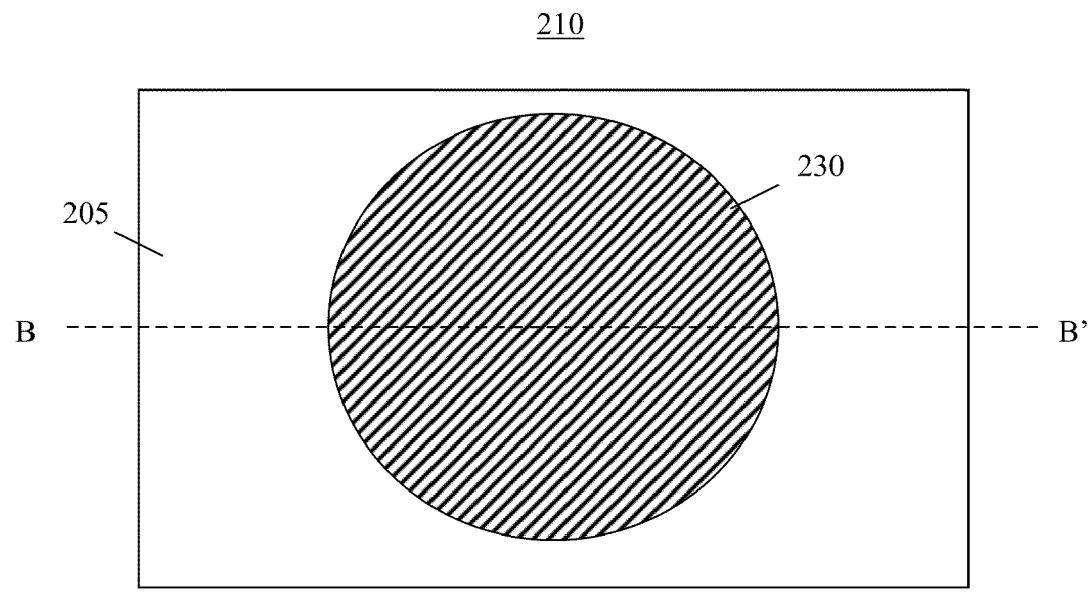
FIG. 2A is as top plan view illustrating a membrane resonant element of a coupled transducer device, according to a representative embodiment.
Figure 2B:
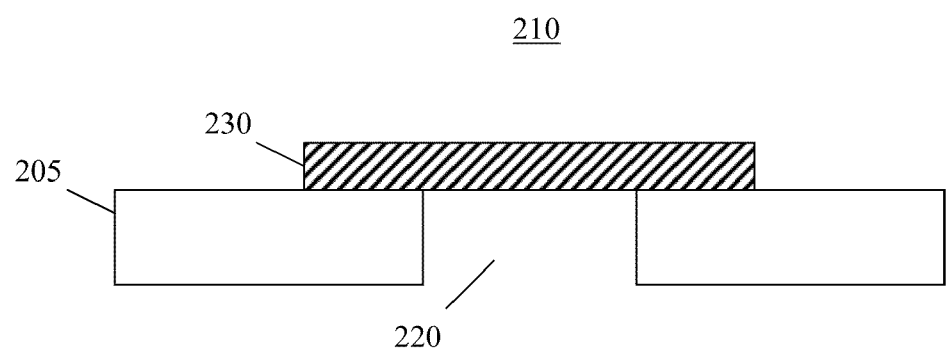
FIG. 2B is a cross-sectional diagram illustrating a membrane resonant element of a coupled transducer device, according to a representative embodiment.

FIG. 2A is as top plan view illustrating a resonant element of a coupled transducer device, which includes a thin plate or membrane, according to a representative embodiment. FIG. 2B is a cross-sectional diagram illustrating the resonant element of a coupled transducer device depicted in FIG. 2A, taken along line B-B', according to a representative embodiment.

Referring to FIGS. 2A and 2B, resonant element 210 includes substrate 205, on which thin plate or membrane 230 is stacked, without a transducer structure. In the depicted embodiment, the membrane 230 is substantially circular in shape, although in alternative embodiments, the membrane 230 may be formed in different shapes, such as ovals, squares, rectangles and the like, without departing from the scope of the present teachings.

As shown in FIG. 2B, the membrane 230 is positioned on the substrate 205 over a cavity 220, which enables mechanical movement of the exposed portion of the membrane 230. The substrate 205 may be formed of various types of materials, including an insulating material, such as glass, sapphire, alumina or the like, or any semiconductor material compatible with semiconductor processes, such as silicon, GaAs, InP, or the like. The membrane 230 may also be formed of various types of materials compatible with semiconductor processes, including polysilicon, silicon nitride, silicon carbide, boron silicate glass or the like. The membrane 230 is thin enough to enable mechanical movement or vibrations in response to pressure waves, e.g., acoustic signals. For example, the membrane 230 may be about 0.5-2 microns thick at the portion exposed over the cavity 220 in order to vibrate at ultrasonic frequencies, although the thickness may vary to provide unique benefits for any particular situation or to meet application specific design requirements of various implementations, as would be apparent to one skilled in the art.

As stated above, according to various embodiments, resonant elements, such as representative resonant elements 110 and 210, are combined in various configurations to share a coupling cavity or a mechanical coupling, such that the two or more coupled resonant elements (referred to as a coupled transducer device) has a modified oscillation behavior, including a modified frequency response, different from that of each of the individual resonant elements. The frequency response of the resonant element combination may therefore be engineered to provide specific benefits or to meet application specific design requirements of various implementations. According to various embodiments, any number or type of resonant elements may be combined in alternative ways to share a coupling cavity, without departing from the scope of the present teachings. FIGS. 3A-6B provide specific non-limiting examples, using combinations of the representative resonant elements 110 and/or 120, as discussed below.

Figure 3A:
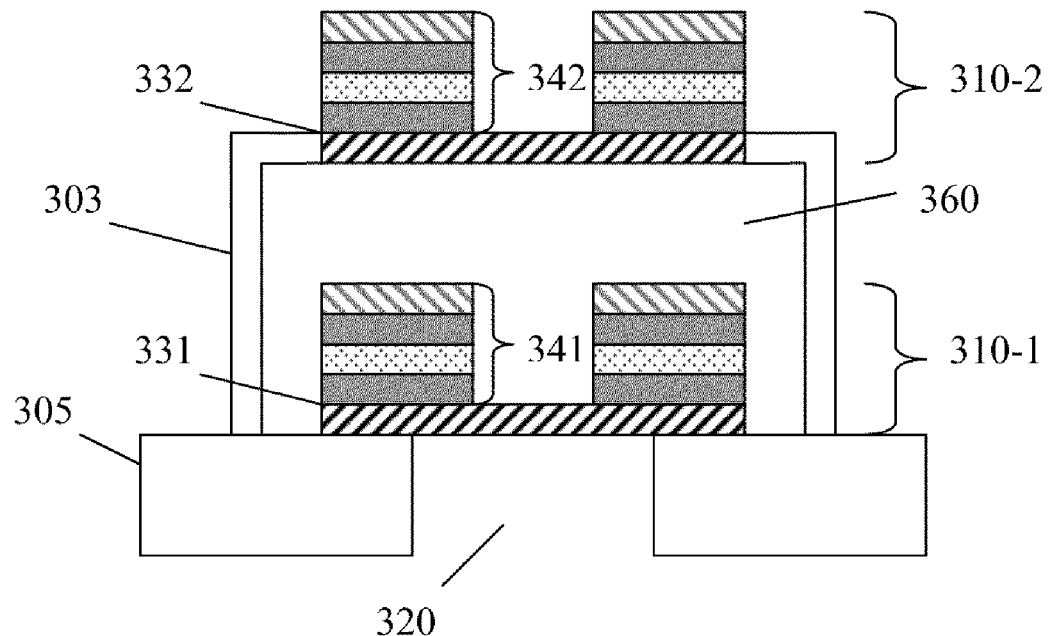
FIGS. 3A and 3B are cross-sectional diagrams illustrating vertically arranged coupled transducer devices, according to representative embodiments.
Figure 3B:
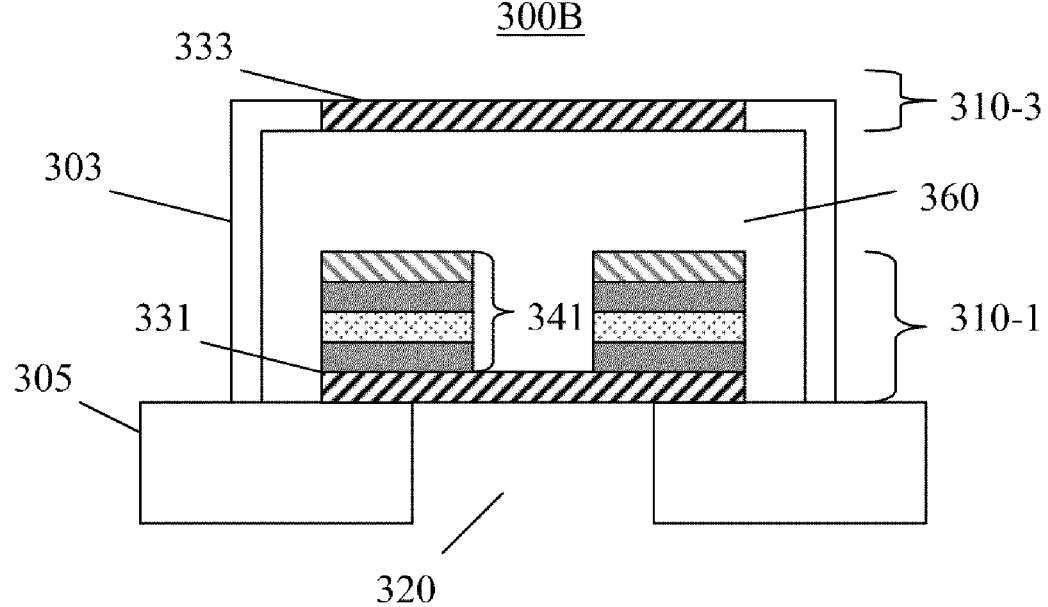

FIGS. 3A and 3B are cross-sectional diagrams illustrating vertically arranged coupled transducer devices, according to representative embodiments.

Referring FIG. 3A, coupled transducer device 300A includes two vertically stacked resonator elements 310-1 and 310-2, and a coupling cavity 360 formed between the vertically stacked resonator elements 310-1 and 310-2. The bottom resonator element 310-1 includes transducer structure 341 stacked on membrane 331, and the top resonator element 310-2 includes transducer structure 342 stacked on membrane 332. The resonator elements 310-1 and 310-2 are thus configured to send or receive acoustic signals through the ambient environment, as well as through the coupling cavity 360. In the depicted embodiment, the transducer structures 341, 342 and the corresponding membranes 331, 332 are substantially the same as the transducer structure 140 and the membrane 130 discussed above with reference to FIGS. 1A and 1B. The vertical arrangement of the resonator elements 310-1, 310-2 and the coupling cavity 360 enables efficient use of space on the wafer (e.g., the substrate 305).

The bottom resonator element 310-1 is arranged over cavity 320 of the substrate 305, which enables mechanical movement or oscillation of the exposed portion of the membrane 331. The substrate 305 may be formed of various types of materials, including glass, sapphire, alumina, silicon, GaAs, InP or the like. The top resonator element 310-2 is arranged on support structure 303 above and substantially in alignment with the bottom resonator element 310-1.

The support structure 303 includes vertical walls extending from the top surface of the substrate 305 and a horizontal top surface, which includes and/or supports the membrane 332 of the top resonator element 310-2. The coupling cavity 360 is formed by the inside surface of the support structure 303 and the top surface of the substrate 305, as well as top and side portions of the first resonant element 310-1 and the exposed bottom portion of the second resonant element 310-2. The coupling cavity 360 may include a vent (not shown), for example, traversing a portion of the support structure 303 or the substrate 305. The vent creates a semi-sealed cavity, which provides pressure equalization and otherwise allows for pressure changes in the environment.

In an embodiment, the support structure 303 is formed of the same material as the membrane 332, such as polysilicon, silicon nitride, silicon carbide, boron silicate glass or the like, in which case the support structure 303 may be one integrated piece, e.g., as discussed below with reference to FIGS. 7E-7I. Mechanical movement of the membrane 332 is enabled by the coupling cavity 360 and the center opening of the transducer structure 342. Alternatively, the vertical walls and an outer peripheral portion of the horizontal top surface of the support structure 303 may be formed from a different material than the membrane 332, in which case the membrane 332 may be stacked on a horizontal top surface of the support structure 303 over an opening formed therein (e.g., substantially the same size and shape as the opening of the cavity 320) or attached to the edges of the opening, enabling mechanical movement of an exposed portion of the membrane 332 over the coupling cavity 360. The support structure 303 may be formed, for example, using sacrificial layer semiconductor processes or through a microcap process, an example of which is described in U.S. patent application Ser. No. 12/430,966, filed Apr. 28, 2009, the subject matter of which is hereby incorporated by reference.

Referring FIG. 3B, coupled transducer device 300B includes two vertically stacked resonator elements 310-1 and 310-3, and a coupling cavity 360 formed between the vertically stacked resonator elements 310-1 and 310-3. The bottom resonator element 310-1 includes transducer structure 341 stacked on membrane 331, and the top resonator element 310-3 includes only membrane 333. In the depicted embodiment, the transducer structure 341 and the membranes 331, 333 are substantially the same as the transducer structure 140 and the membrane 130 discussed above with reference to FIGS. 1A and 1B, and the membrane 230 discussed above with reference to FIGS. 2A and 2B. The vertical arrangement of the resonator elements 310-1, 310-3 and the coupling cavity 360 enables efficient use of space on the wafer (e.g., the substrate 305).

The bottom resonator element 310-1 is arranged over cavity 320 of substrate 305, as discussed above with reference to FIG. 3A. The top resonator element 310-3 is arranged on support structure 303 above and substantially in alignment with the bottom resonator element 310-1. The support structure 303 includes vertical walls extending from the top surface of the substrate 305 and a horizontal top surface, which includes and/or supports the membrane 333 of the top resonator element 310-3. In an embodiment, the support structure 303 is formed of the same material as the membrane 333, such as polysilicon, silicon nitride, silicon carbide, boron silicate glass, or the like, in which case the support structure 303 may be one integrated piece. Alternatively, the vertical walls and an outer peripheral portion of the horizontal top surface of the support structure 303 may be formed from a different material than the membrane 333, in which case the membrane 333 may be stacked on a horizontal top surface of the support structure 303 over an opening formed therein (e.g., substantially the same size and shape as the opening of the cavity 320) or attached to the edges of the opening, enabling mechanical movement of an exposed portion of the membrane 333 over the coupling cavity 360.

In FIGS. 3A and 3B, pressure waves (e.g., acoustic signals) formed by oscillations of the bottom resonator element 310-1 and the top resonator element 310-2 or 310-3 are translated through the coupling cavity 360, thus affecting the oscillation behavior of one another. Accordingly, the frequency response and other characteristics of the coupled transducer devices 300A and 300B are different from those of either the bottom resonator element 310-1 and the top resonator element 310-2, 310-3. The substantially enclosed nature of the coupling cavity 360 enables a relatively strong coupling response.

Figure 4A:
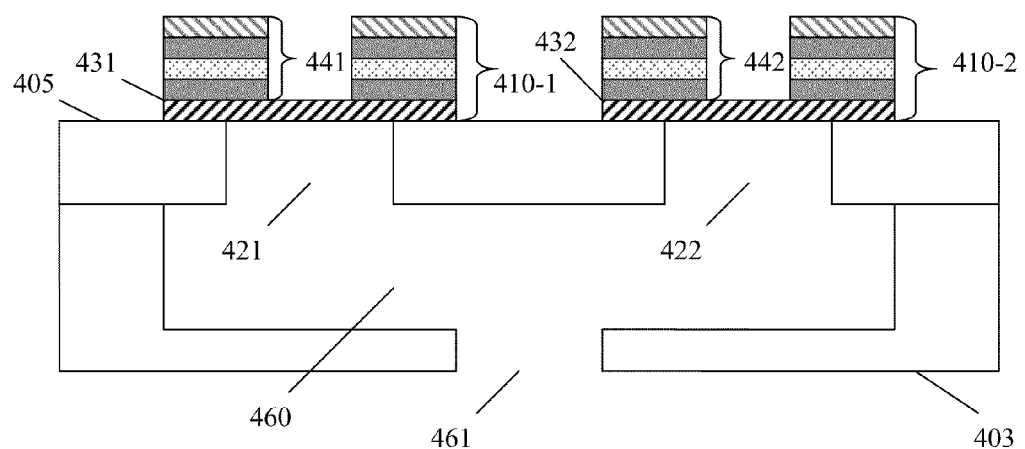
FIGS. 4A and 4B are cross-sectional diagrams illustrating horizontally arranged coupled transducer devices, according to representative embodiments.
Figure 4B:
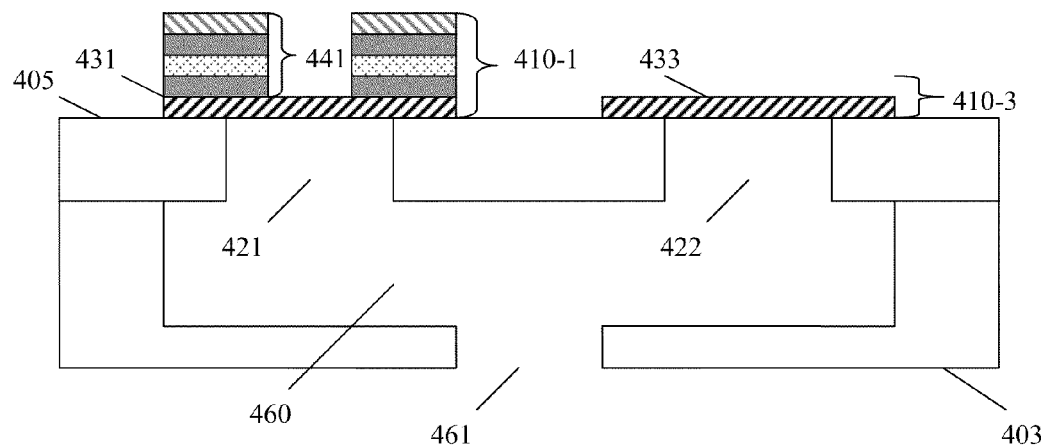

FIGS. 4A and 4B are cross-sectional diagrams illustrating horizontally arranged coupled transducer devices, according to representative embodiments.

Referring FIG. 4A, coupled transducer device 400A includes two adjacent, horizontally arranged resonator elements 410-1 and 410-2, and a coupling cavity 460 extending beneath cavities 421 and 422 of the resonator elements 410-1 and 410-2. The left resonator element 410-1 includes transducer structure 441 stacked on membrane 431, and the right resonator element 410-2 includes transducer structure 442 stacked on membrane 432. Mechanical movements or oscillations of the membranes 431 and 432 are enabled by the cavities 421 and 422, respectively. The resonator elements 410-1 and 410-2 are thus configured to send or receive acoustic signals through the ambient environment, as well as through the coupling cavity 460. In the depicted embodiment, the transducer structures 441, 442 and the corresponding membranes 431, 432 are substantially the same as the transducer structure 140 and the membrane 130 discussed above with reference to FIGS. 1A and 1B.

The left resonator element 410-1 is arranged over the cavity 421 of substrate 405 and the right resonator element 410-2 is arranged over the cavity 422 of substrate 405, which enables mechanical movement of the exposed portions of the membranes 431, 432, respectively. The substrate 405 may be formed of various types of materials, such as glass, sapphire, alumina, silicon, GaAs, InP or the like. Also, in another embodiment, the membranes 431 and 432 may be formed of the same membrane layer, extending continuously below the transducer structures 441 and 442.

The coupling cavity 460 is defined by the substrate 405 and cavity structure 403 formed beneath the substrate 405. The cavity structure 403 includes vertical walls extending from the bottom surface of the substrate 405 and a horizontal bottom portion, which defines a coupling cavity opening 461. In an embodiment, the cavity structure 403 is formed of the same material as the substrate 405, such as glass, sapphire, alumina, silicon, GaAs, InP or the like, in which case the cavity structure 403 and the substrate 450 may be one piece. The cavity structure 403 may be formed, for example, using sacrificial layer semiconductor processes or through a microcap process, an example of which is described in U.S. patent application Ser. No. 12/430,966, filed Apr. 28, 2009, the subject matter of which is hereby incorporated by reference.

In an embodiment, a gas permeable screen or mesh (not shown) may cover the coupling cavity opening 461 in order to provide additional protection of the internal components, including the exposed lower surfaces of the membranes 431 and 432. For example, the screen or mesh may include multiple apertures sufficiently large to allow exposure to the ambient environment, yet small enough to limit the amount of debris, contaminates and moisture that can enter the coupling cavity opening 461.

Referring FIG. 4B, coupled transducer device 400B includes two adjacent, horizontally arranged resonator elements 410-1 and 410-3, and a coupling cavity 460 extending beneath cavities 421 and 422 of the resonator elements 410-1 and 410-3. The left resonator element 410-1 includes transducer structure 441 stacked on membrane 431, and the right resonator element 410-3 includes only membrane 433, with no transducer structure. Mechanical movements or oscillations of the membranes 431 and 433 are enabled by the cavities 421 and 422, respectively. In the depicted embodiment, the transducer structure 441 and the membranes 431, 433 are substantially the same as the transducer structure 140 and the membrane 130 discussed above with reference to FIGS. 1A and 1B, and the membrane 230 discussed above with reference to FIGS. 2A and 2B.

The left resonator element 410-1 is arranged over the cavity 421 of substrate 405 and the right resonator element 410-3 is arranged over the cavity 422 of substrate 405, which enables mechanical movement of the exposed portions of the membranes 431, 433, as discussed above with reference to FIG. 4A. Also, in another embodiment, the membranes 431 and 433 may be formed of the same membrane layer, extending continuously over the top surface of the substrate 405, across opening of both cavities 421, 422 and below the transducer structure 441. The coupling cavity 460 is defined by the substrate 405 and cavity structure 403 formed beneath the substrate 405, as discussed above with reference to FIG. 4A.

In FIGS. 4A and 4B, pressure waves (e.g., acoustic signals) formed by oscillations of the left resonator element 410-1 and the right resonator element 410-2 or 410-3 are translated through the coupling cavity 460, thus affecting the oscillation behavior of one another. Accordingly, the frequency response and other characteristics of the coupled transducer devices 400A and 400B are different from those of either the left resonator element 410-1 and the right resonator element 410-2, 410-3.

Figure 5A:
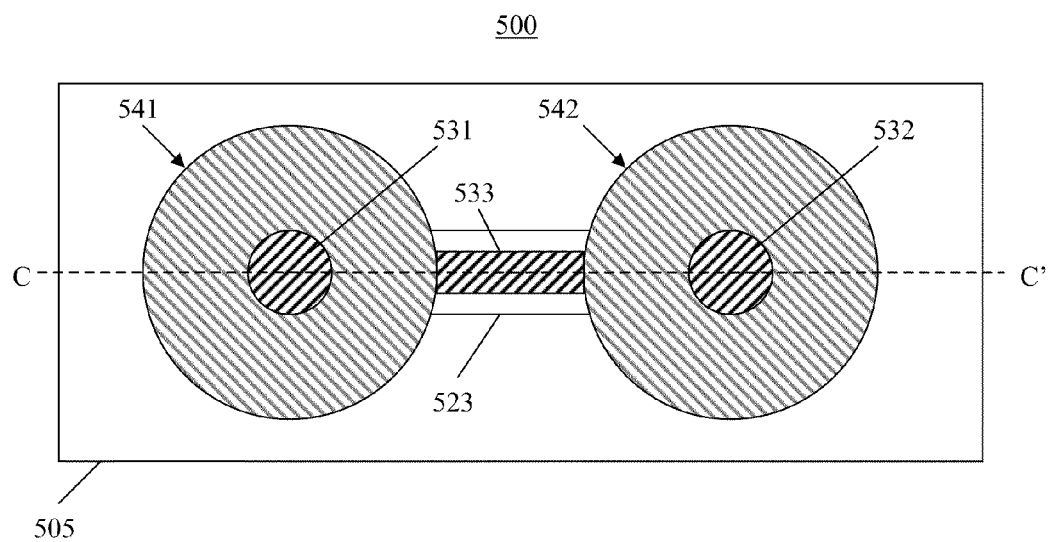
FIG. 5A is as top plan view illustrating a horizontally arranged coupled transducer device and coupling beam, according to a representative embodiment.
Figure 5B:
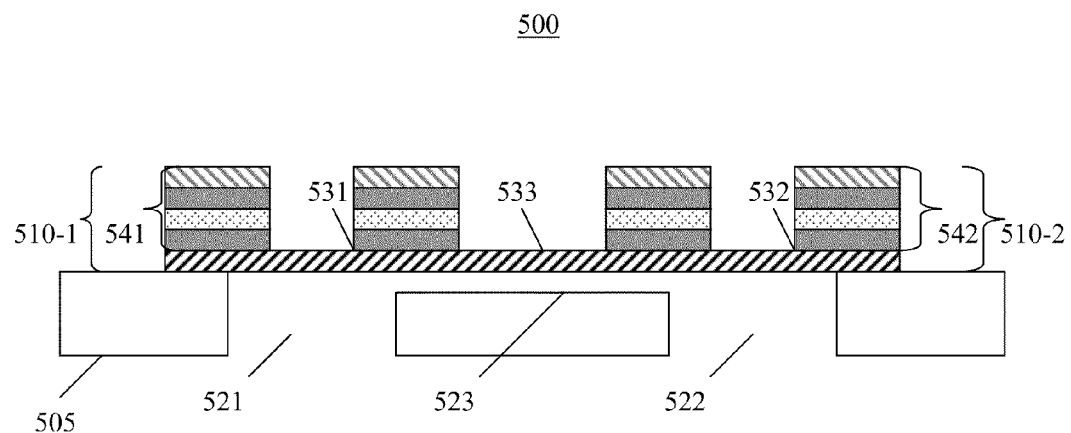
FIG. 5B is a cross-sectional diagram illustrating a horizontally arranged coupled transducer device and coupling beam, according to a representative embodiment.

FIG. 5A is as top plan view illustrating a horizontally arranged coupled transducer device and coupling beam, according to a representative embodiment. FIG. 5B is a cross-sectional diagram illustrating the horizontally arranged coupled transducer device of FIG. 5A, taken along line C-C', according to a representative embodiment.

Referring FIGS. 5A and 5B, coupled transducer device 500 includes two adjacent, horizontally arranged resonator elements 510-1 and 510-2. However, instead of a coupling cavity, in which acoustic signals are coupled in a gas coupling medium (e.g., air), the resonator elements 510-1 and 510-2 are coupled mechanically through a solid element, depicted as rectangular bar or coupling beam 533. The coupling beam 533 works similarly to an air coupling medium, such as coupling cavities 360 and 460, in order to couple resonant elements, accounting for differences in acoustic signal propagation. However, the coupling beam 533 may be formed in any shape, such as a rectangle, serpentine, wedge, or the like, to provide unique benefits for any particular situation or to meet application specific design requirements of various implementations, as would be apparent to one skilled in the art.

The coupling beam 533 extends between and contacts the membranes 531 and 532 of the resonator elements 510-1 and 510-2. In the depicted embodiment, the coupling beam 533 is formed from the same layer as the membranes 531 and 532, and thus is made of the same material, e.g., polysilicon, silicon nitride, silicon carbide, boron silicate glass, or the like.

Alternatively, the coupling beam 533 may be formed separately from the membranes 531 and 532, in which case the coupling beam 533 may be formed of the same or different material as the membranes 531 and 532. The coupling beam 533 may be a hanging beam, for example, positioned over a gap 523 (e.g., air gap), which is formed between a bottom surface of the coupling beam 533 and a top surface of a center portion of the substrate 505. The gap 523 may be formed as a recess or "swimming pool" in the substrate 505, for example, using sacrificial layer semiconductor processes.

Referring to FIG. 5B, the left resonator element 510-1 includes transducer structure 541 stacked on membrane 531, and the right resonator element 510-2 includes transducer structure 542 stacked on membrane 532. Mechanical movements of the membranes 531 and 532 are enabled by the cavities 521 and 522, respectively, and translated to one another via the coupling beam 533. The resonator elements 510-1 and 510-2 are thus configured to send or receive acoustic signals through the ambient environment, as well as through the coupling beam 533. In the depicted embodiment, the transducer structures 541, 542 and the corresponding membranes 531, 532 are substantially the same as the transducer structure 140 and the membrane 130 discussed above with reference to FIGS. 1A and 1B.

The left resonator element 510-1 is arranged over the cavity 521 of substrate 505 and the right resonator element 510-2 is arranged over the cavity 522 of substrate 505, which enables mechanical movement of the exposed portions of the membranes 531, 532, respectively. The substrate 505 may be formed of various types of materials, such as glass, sapphire, alumina, silicon, GaAs, InP, or the like. Also, in another embodiment, the membranes 531 and 532 may be formed of the same membrane layer, extending continuously below the transducer structures 541 and 542 and including the coupling beam 533, as stated above.

In an embodiment, a gas permeable screens or meshes (not shown) may cover the openings of cavities 521 and 522 in order to provide additional protection of the internal components, including the exposed lower surfaces of the membranes 531 and 532. For example, the screen or mesh may include multiple apertures sufficiently large to allow exposure to the ambient environment, yet small enough to limit the amount of debris, contaminates and moisture that can enter the openings of cavities 521 and 522.

Figure 6A:
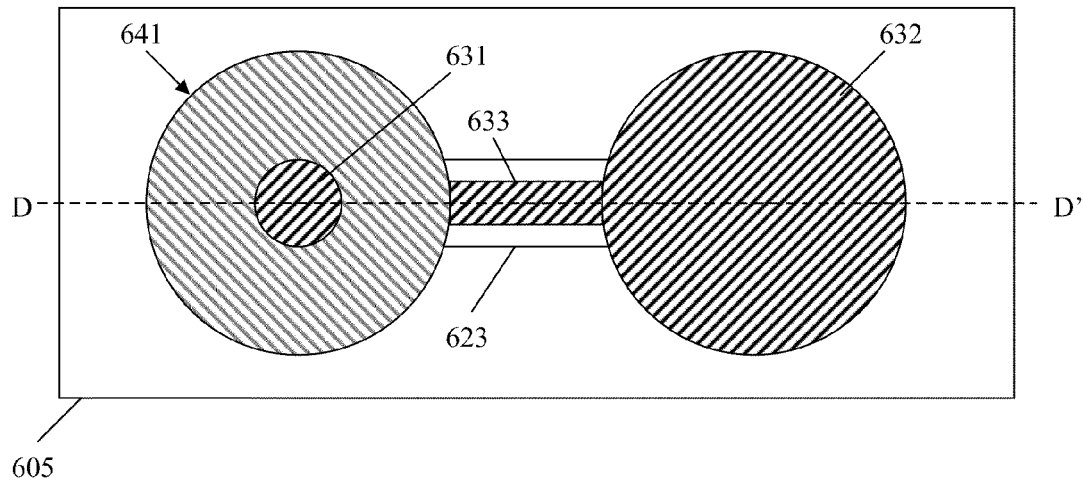
FIG. 6A is as top plan view illustrating a horizontally arranged coupled transducer device and coupling beam, according to a representative embodiment.
Figure 6B:
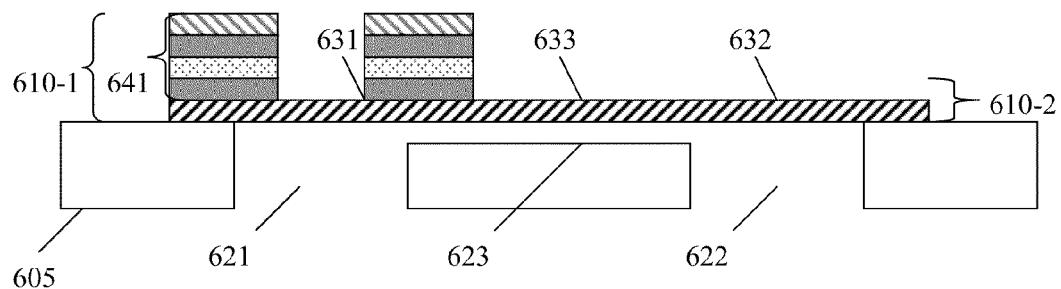
FIG. 6B is a cross-sectional diagram illustrating a horizontally arranged coupled transducer device and coupling beam, according to a representative embodiment.

FIG. 6A is as top plan view illustrating a horizontally arranged coupled transducer device and coupling beam, according to a representative embodiment. FIG. 6B is a cross-sectional diagram illustrating the horizontally arranged coupled transducer device of FIG. 6A, taken along line D-D', according to a representative embodiment.

Referring FIGS. 6A and 6B, coupled transducer device 600 includes two adjacent, horizontally arranged resonator elements 610-1 and 610-2, which are coupled mechanically through a solid element, depicted as rectangular bar or coupling beam 633, instead of a coupling cavity. As discussed above with reference to coupling beam 533 in FIGS. 5A and 5B, the coupling beam 633 may be formed in any shape, such as a rectangle, serpentine, wedge, or the like, to provide unique benefits for any particular situation or to meet application specific design requirements of various implementations, as would be apparent to one skilled in the art. Also, the coupling beam 633 extends between and contacts the membranes 631 and 632 of the resonator elements 610-1 and 610-2. In the depicted embodiment, the coupling beam 633 is formed from the same layer as the membranes 631 and 632, and thus is made of the same material, e.g., polysilicon, silicon nitride, silicon carbide, boron silicate glass, or the like.

Alternatively, the coupling beam 633 may be formed separately from the membranes 631 and 632, in which case the coupling beam 633 may be formed of the same or different material as the membranes 631 and 632. The coupling beam 632 is positioned over a gap 623 (e.g., air gap), which is formed between a bottom surface of the coupling beam 633 and a top surface of a center portion of the substrate 605, as discussed above.

The left resonator element 610-1 includes transducer structure 641 stacked on membrane 631, as discussed above with reference to left resonator element 510-1. However, the right resonator element 610-3 includes only membrane 632 (with no stacked transducer structure). Mechanical movements of the membranes 631 and 632 are enabled by the cavities 621 and 622, respectively, and translated to one another via the coupling beam 633. The resonator elements 610-1 and 610-2 are thus configured to send or receive acoustic signals through the ambient environment, as well as through the coupling beam 633. In the depicted embodiment, the transducer structure 641 and the membranes 631, 632 are substantially the same as the transducer structure 140 and the membrane 130 discussed above with reference to FIGS. 1A and 1B, and the membrane 230 discussed above with reference to FIGS. 2A and 2B.

The left resonator element 610-1 is arranged over cavity 621 of substrate 605 and the right resonator element 610-3 is arranged over cavity 622 of substrate 605, which may be formed of various types of materials, including an insulating material, such as glass, sapphire, alumina or the like, or any semiconductor material compatible with semiconductor processes, such as silicon, GaAs, InP, or the like. Also, in another embodiment, the membranes 631 and 632 may be formed of the same membrane layer, extending continuously below the transducer structure 641 and including the coupling beam 633, as stated above. In an embodiment, a gas permeable screens or meshes (not shown) may cover the openings of cavities 621 and 622 in order to provide additional protection of the internal components, including the exposed lower surfaces of the membranes 631 and 632.

As stated above, the coupled transducer devices of the various representative embodiments (e.g., coupled transducer devices 300A, 300B, 400A, 400B, 500 and 600) may be fabricated in accordance with various techniques compatible with semiconductor processes. A non-limiting example of a fabrication process directed to transducer device 300A depicted in FIG. 3A is provided by FIGS. 7A-7I, using a surface micromachining approach, according to various embodiments. It is understood that all or part of the process depicted in FIGS. 7A-7I may be applied to the fabrication of the other coupled transducer devices 300B, 400A, 400B, 500 and 600 discussed herein.

Figure 7A:
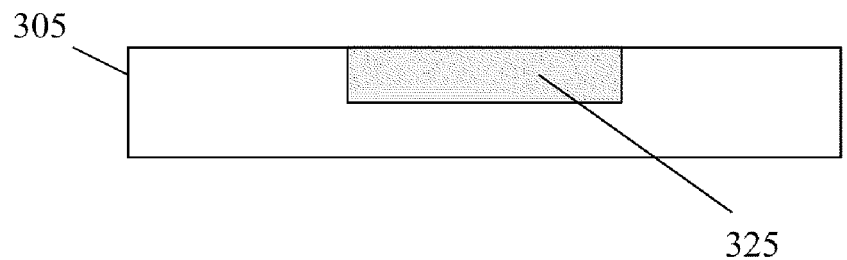
FIGS. 7A-7I are cross-sectional diagrams illustrating steps in a fabrication process of a representative vertically arranged coupled transducer device, according to a representative embodiment.

Referring to FIG. 7A, a "swimming pool" or recess 325 is formed in a top surface of the substrate 305, using by machining or by chemically etching the substrate 305 using photolithography, although various alternative techniques may be incorporated. In an embodiment, the recess 325 may be about 2-3 microns deep, for example. The recess is filled with a phosphosilicate glass (PSG) film, for example. A chemical mechanical polish (CMP) may be performed to create a planar top surface.

Figure 7B:
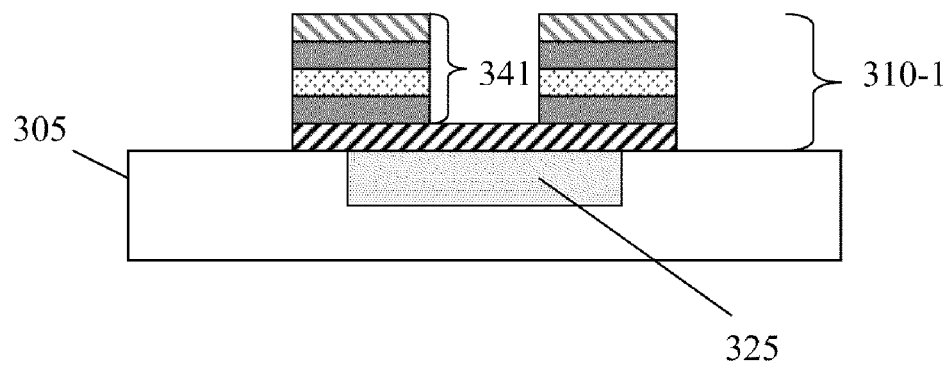

Referring to FIG. 7B, the resonant element 310-1 is formed on the top surfaces of the substrate 305 and PSG filled recess 325. As discussed above, the resonant element 310-1 includes membrane 331 and stacked transducer structure 341. The resonant element 310-1 may be fabricated by applying a layer of polysilicon, silicon nitride, silicon carbide, boron silicate glass or the like, to the top surfaces of the substrate 305 and PSG filled recess 325 as the membrane 331. The transducer structure 341 may then be formed by applying a layer of an electrically conductive material, such as molybdenum, tungsten or aluminum or the like, as a first electrode, applying a piezoelectric thin film, such as AlN or ZnO, as a piezoelectric layer, applying another layer of the electrically conductive material as a second electrode, and optionally applying a passivation layer. The conductive layers may be respectively patterned, for example, using photolithography, although various alternative techniques may be incorporated, to provide the desired shapes of the bottom and top electrodes.

Figure 7C:
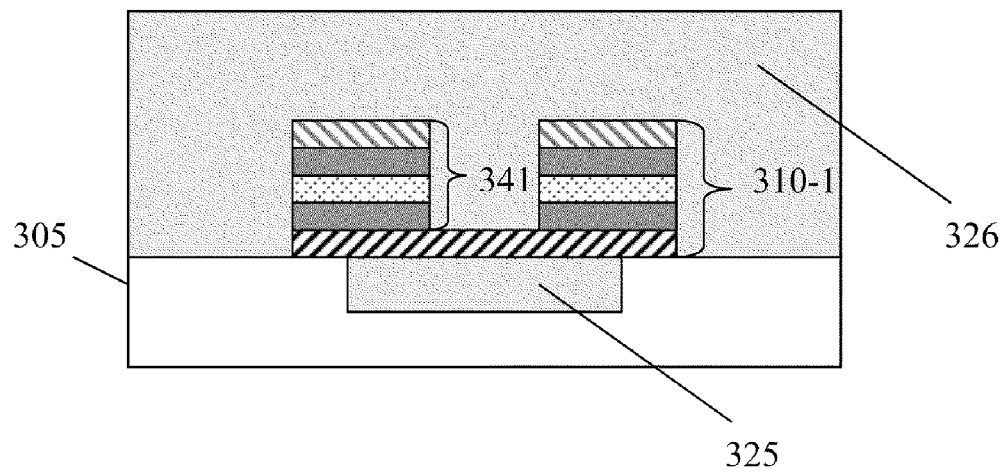
Figure 7D:
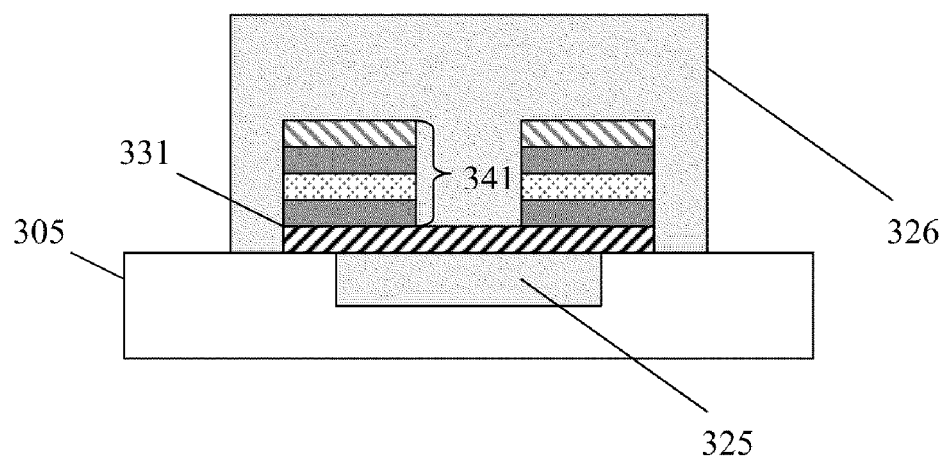

Referring to FIG. 7C, the substrate 305 and the resonant element 310-1 are covered with PSG layer 326, which is then polished using CMP to create a planar top surface. The PSG layer 326 is masked and etched to the desired dimensions, as shown in FIG. 7D.

Figure 7E:
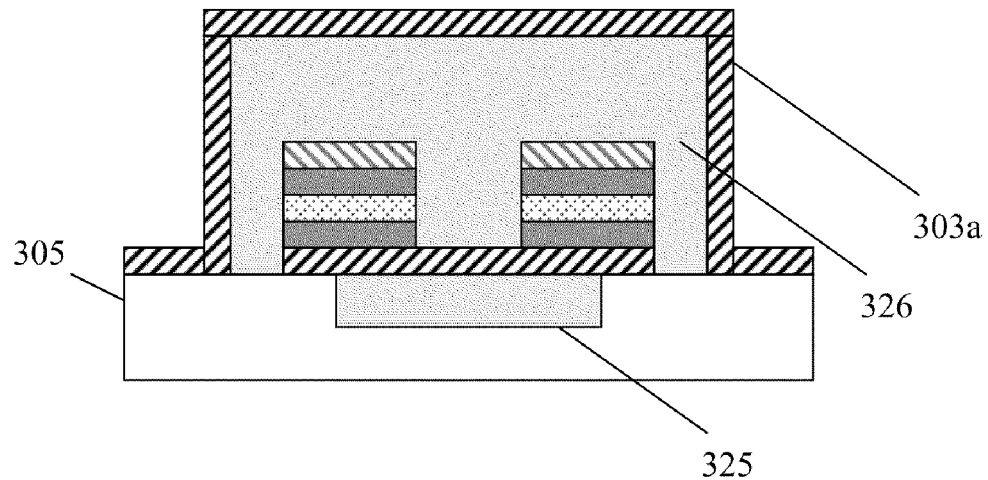
Figure 7F:
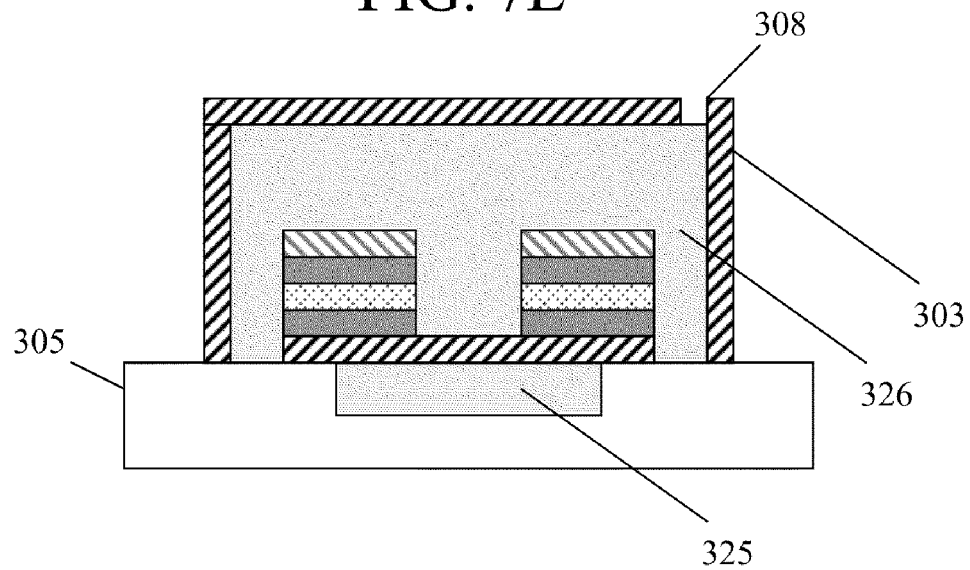

Referring to FIG. 7E, a membrane material 303a, such as polysilicon, silicon nitride, silicon carbide, boron silicate glass or the like, is deposited over the PSG layer 326 and the substrate 305. In an embodiment, the membrane material 303a is the same material used to form the membrane 331, and may be deposited using a plasma-enhanced chemical-vapor deposition (PECVD) process, for example. Unwanted membrane material 303a is removed by etching, as shown in FIG. 7F, to form the membrane layer (or support structure) 303. The etching includes removal of excess membrane material 303a from the top surface of the substrate 305, as well as forming etch hole 308. The etching may include chemically etching the membrane material 303a using photolithography, although various alternative techniques may be incorporated.

Figure 7G:
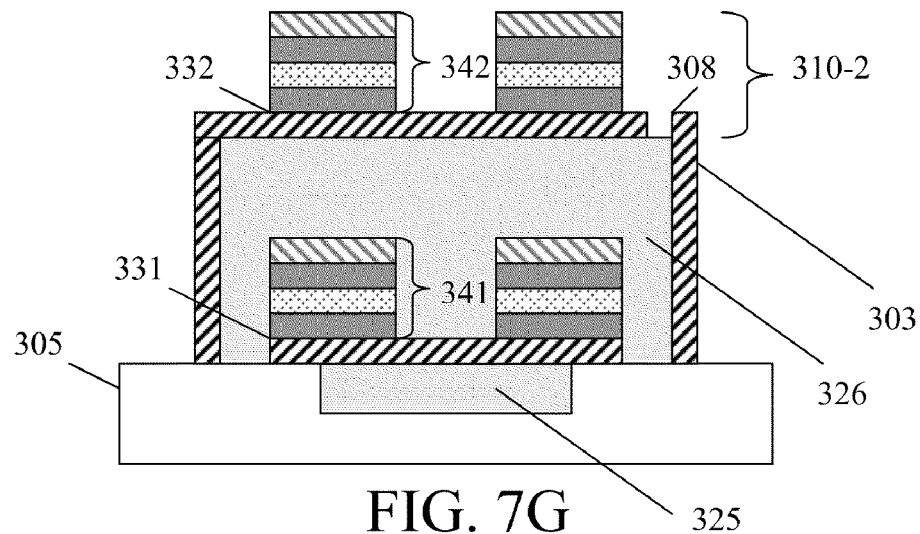

Referring to FIG. 7G, the resonant element 310-2 is formed on the top surface of the membrane material 303. As discussed above, the resonant element 310-2 includes membrane 332 and stacked transducer structure 342, which is fabricated according to substantially the same process described above with respect to the transducer structure 341. In the depicted embodiment, the membrane 332 is integral with the membrane layer 303, and therefore need not be formed in separate step.

Figure 7H:
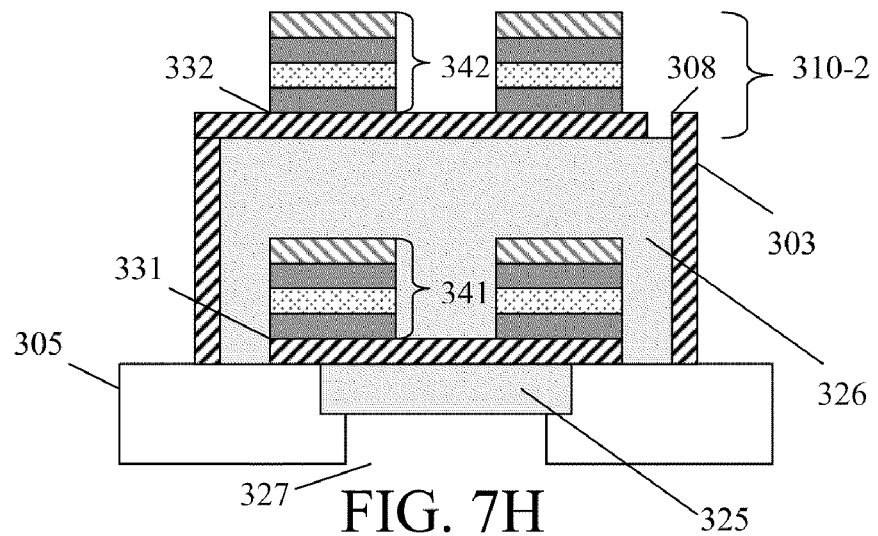
Figure 7I:
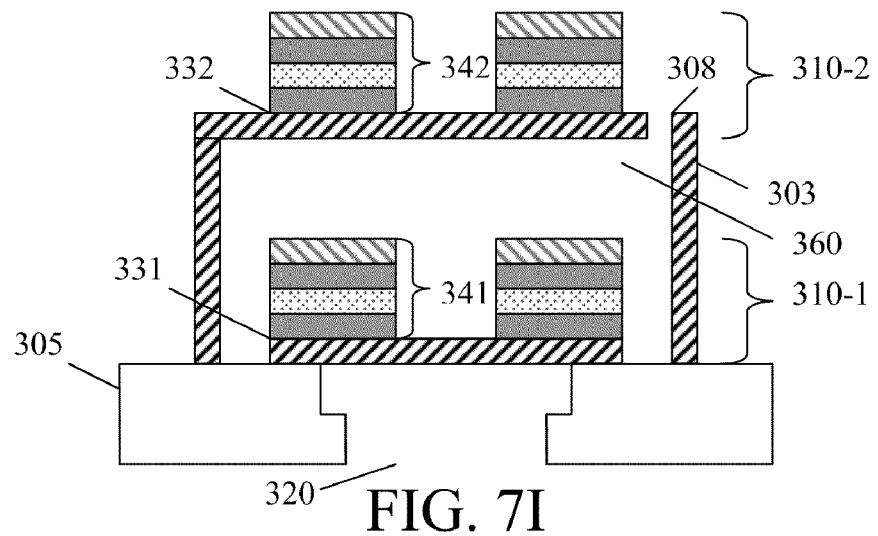

Referring to FIG. 7H, back side etching is performed on a bottom surface of the substrate 305 to form preliminary cavity 327 directly below the PSG filled recess 325, which serves as an etch stop. The back side etch may include using a dry etch process, such as a Bosch process, for example, although various alternative techniques may be incorporated without departing from the scope of the present teachings. The PSG material of the recess 325 and the PSG layer 326 is then chemically released or etched, for example, using a wet etch process including HF etch solution, for example. After the PSG material has been removed, cavity 320 is formed through the substrate 305 (by merging the recess 325 and the preliminary cavity 327) and the coupling cavity 360 is formed within the membrane layer 303, as shown in FIG. 7I. Also, the etch hole 308 becomes a vent for the coupling cavity 360.

In an embodiment, the contact pads (not shown) may be formed by applying a gold layer to the outer surfaces of the substrate 305 and the membrane layer 303, respectively, and patterning the gold layer, for example, using photolithography, although various alternative techniques may be incorporated. As stated above, the contact pads connect with the first and second electrodes of both transducer structures 341 and 342 by connectors (not shown) formed through corresponding via holes through the substrate 305 and/or the membranes 331 and 332. The via holes may be formed prior to the formation of the transducer structures 341 and 342 and the contact pads, for example, using photolithography, although various alternative techniques may be incorporated. It is understood that, in other embodiments, the number, location and arrangement of the contact pads and corresponding connectors vary to provide unique benefits for any particular situation or to meet application specific design requirements of various implementations, as would be apparent to one skilled in the art.

According to various embodiments, the coupling transducer device eliminates the technical trade off between bandwidth and gain when only one transducer is used. Also, the he coupled transducer device is well suited for time-of-flight measurements that utilize frequency or phase modulation schemes.

The various components, materials, structures and parameters are included by way of illustration and example only and not in any limiting sense. In view of this disclosure, those skilled in the art can implement the present teachings in determining their own applications and needed components, materials, structures and equipment to implement these applications, while remaining within the scope of the appended claims.

The invention claimed is:

1. A transducer device, comprising:
a coupling cavity;
a first resonant element formed over a first cavity and coupled to the coupling cavity via the first cavity, the first resonant element being configured to send or receive acoustic signals; and
a second resonant element formed over a second cavity and coupled to the coupling cavity via the second cavity, the second resonant element being configured to modify a frequency response of the first resonant element via the coupling cavity.

2. The device of claim 1, wherein the first and second resonant elements are vertically stacked, such that the coupling cavity is formed between a top portion of the first resonant element and a bottom portion the second resonant element.

3. The device of claim 2, wherein the first resonant element comprises a first membrane and a first transducer structure arranged on a substrate, a portion of the first membrane extending over the first cavity in the substrate to enable oscillation at a first frequency.

4. The device of claim 3, wherein the first transducer structure comprises a first piezoelectric layer positioned between first and second electrodes.

5. The device of claim 3, wherein the second resonant element comprises a second membrane and a second transducer structure arranged on a support structure extending from a top surface of the substrate, a portion of the second membrane extending over the second cavity in the support structure to enable oscillation at a second frequency, and
wherein at least a portion of the coupling cavity is defined by the support structure and the substrate.

6. The device of claim 5, wherein the first and second transducer stacks comprise annular shapes.

7. The device of claim 5, wherein the first frequency and the second frequency are the same.

8. The device of claim 5, wherein the first frequency and the second frequency are different.

9. The device of claim 3, wherein the second resonant element comprises a second membrane, without a transducer structure, arranged on a support structure extending from a top surface of the substrate, a portion of the second membrane extending over the second cavity in the support structure to enable oscillation at a second frequency, and
wherein at least a portion of the coupling cavity is defined by the support structure and the substrate.

10. The device of claim 1, wherein the first and second resonant elements are arranged horizontally on a substrate, and the coupling cavity is formed below the first and second cavities formed in the substrate corresponding to the first and second resonant elements.

11. The device of claim 10, wherein the first resonant element comprises a first membrane and a first transducer structure arranged on the substrate, a portion of the first membrane extending over the first cavity in the substrate to enable oscillation at a first frequency.

12. The device of claim 11, wherein the second resonant element comprises a second membrane and a second transducer structure arranged on the substrate, a portion of the second membrane extending over the second cavity in the substrate to enable oscillation at a second frequency.

13. The device of claim 12, wherein the first and second membranes are formed from the same layer of membrane material.

14. The device of claim 11, wherein the second resonant element comprises a second membrane, without a transducer structure, arranged on the substrate, a portion of the second membrane extending over the second cavity in the substrate to enable oscillation at a second frequency.

15. A transducer device, comprising:
a substrate defining a plurality of resonator cavities;
a membrane formed on a top surface of the substrate;
a plurality of resonator elements corresponding to the plurality of resonator cavities, the plurality of resonator elements being formed on the membrane over the plurality of resonator cavities, respectively; and
a common coupling cavity configured to couple acoustic signals from the plurality of resonant elements via the plurality of resonator cavities.

16. The transducer device of claim 15, wherein at least one of the plurality of resonator elements comprises a transducer structure stacked on the membrane.

17. The transducer device of claim 15, further comprising:
a cavity structure formed on a bottom surface of the substrate, the cavity structure defining the common coupling cavity.

18. The transducer device of claim 15, wherein the substrate comprises at least one of silicon, gallium arsenide (GaAs), and indium phosphide (InP), and
wherein the membrane comprises at least one of polysilicon, silicon nitride, silicon carbide, and boron silicate glass.

* * * * *